United States Patent [19]

Mascolo et al.

[11] Patent Number: 5,078,046
[45] Date of Patent: Jan. 7, 1992

[54] AIR TREATMENT APPARATUS AND METHOD

[76] Inventors: Dennis G. Mascolo, 157 N. Helm Rd.; Frank Giuliano, 132 Brinker Rd., both of Barrington Hills, Ill. 60010; John A. Young, 355 High Rd., Cary, Ill. 60013

[21] Appl. No.: 400,146

[22] Filed: Nov. 24, 1989

[51] Int. Cl.5 .................. B60H 3/02; F24F 13/00
[52] U.S. Cl. .................. 454/157; 261/DIG. 17; 454/148; 454/161; 454/75
[58] Field of Search ............ 98/2.11, 109, 105; 422/111, 124; 261/DIG. 4, DIG. 15, DIG. 17

[56] References Cited

U.S. PATENT DOCUMENTS

| | | | |
|---|---|---|---|
| 2,504,278 | 4/1948 | Read et al. | 261/DIG. 15 |
| 3,158,081 | 11/1964 | Frost | 98/109 |
| 4,159,672 | 7/1976 | Garguilo et al. | 261/DIG. 17 |
| 4,309,382 | 1/1982 | Miller | 98/2.11 |
| 4,867,045 | 9/1989 | Freedman | 98/2.11 |
| 4,913,034 | 4/1990 | Ripple et al. | 261/DIG. 17 |

FOREIGN PATENT DOCUMENTS

| | | | |
|---|---|---|---|
| 2218929 | 2/1973 | France | 261/DIG. 17 |
| 2448930 | 2/1979 | France | 422/124 |

Primary Examiner—Albert J. Makay
Assistant Examiner—William C. Doerrler
Attorney, Agent, or Firm—James T. FitzGibbon

[57] ABSTRACT

An air treatment system for a vehicle or other habitable structure. The apparatus includes a supply of treating fluid, a pump and spray nozzle arrangement, and a control system. The spray nozzle discharges the treating liquid in an atomized condition within an air circulation conduit, and the control system insures that there is air flow taking place in the conduit before atomization begins and that air flow is still continuing after cessation of atomization. The sequences is insured by a logic control and the pump is actuated through a timer and relay arrangement. An automatic conditioned responsive mode of operation can also be provided.

5 Claims, 2 Drawing Sheets

AIR TREATMENT APPARATUS AND METHOD

The present invention relates generally to air treatment apparatus, and more particularly, to a low cost apparatus for treatment of fluent air in household, commercial and automotive applications. By "treatment" is meant supplying deodorizing or air freshening chemicals, particular scents, and in some cases, chemicals for air cleaning such as fungicides, mildewicides or the like.

In keeping with the invention, the apparatus may be used in connection with automotive application, such as with automobiles and light trucks, for example, or may used in a home or business environment. Basically, the apparatus, either automatically or under the control of an operator, delivers a pre-selected volume of an air treating liquid in atomized form into an air stream which is directed into the environment to be controlled.

From the standpoint of operation, the apparatus may be what is termed "manual", insofar as both the timing and the duration of the introduction of atomized liquid into the air stream is carried out manually. Under such circumstances, auxiliary functions such as the determination that positive air flow is present may be made manually or may be a condition which must be positively sensed in order to enable manual operation to take place.

In one form, a semi-automatic mode of operation may be utilized. In such a case, the sequence of injection or atomization is manually initiated, with a control mechanism insuring that either a fan control or other means of air circulation is to be enabled or, if previously enabled, will remain enabled for the duration of the atomization, and preferably for at least for some time thereafter In such a semi-automatic mode, the operating sequence may call for a delay between the time injection is requested and the time that conditions occur to permit such injection in keeping with the "logic" applicable to that form of apparatus.

In the semi-automatic mode, it is also possible to impose other conditions of logic on the operation of the system, so as to disable the system at or below a given threshold temperature, for example.

Still further, the invention is capable of being embodied a fully automatic device, wherein the air treatment is initiated by means independent of the operator. This may include, in the case of a household operation, cycle initiation by way of a preset timer, or by detection of certain conditions. Likewise, in an automotive environment, an apparatus may also be enabled by a timer or might otherwise be initiated by a certain action such as starting the vehicle. Typically, in this case, when the vehicle is first started, a delay circuit is enabled, and after a suitable time, the treatment cycle is initiated, again assuming that the proper conditions for injection or atomization are present in the system.

As a further refinement, the system may be initially enabled, or may have certain of its operating parameters varied, in a feedback relation to a detected condition. For example, a detection of cigarette smoke or the like may initiate a cycle, or the presence or intensity of cigarette smoke in a portion of the controlled atmosphere may insure that larger and/or more frequent "shot sizes" of the treatment liquid are entrained into the air stream.

An important feature of the invention is an operating sequence which is characterized by simplicity, and the use of materials which are highly reliable and available at low cost. In this connection, appropriate components may be selected from existing sources, or suitable components may be constructed at low cost use in the apparatus of the invention.

Another optional feature is that any one of the foregoing systems may include reservoirs for more than one treating liquid, enabling the user to select among deodorizing- or fragrance-imparting cycles, adding bacteriostatic, or other agents to the air stream, with or without the addition of deodorizing and/or fragrance imparting liquids By "treating liquid" as used herein is meant any liquid not naturally occurring in air, such as liquid water or water vapor which is ordinarily present in air.

In a preferred form, the apparatus requires at least one reservoir for a treating liquid, a simple pump and motor unit and means for energizing the motor to actuate the pump, a conduit, and a plenum insert unit comprising a spray nozzle and means for connecting to nozzle and the pump to the liquid conduit. Depending upon the adaptation of the original equipment in an automobile or residence, for example, or as an aftermarket item, the configuration of these parts may be selected to achieve the desired objective. Other auxiliary functions as described above may be provided by electronic or mechanical timers, and simple operational logic may be provided either by a programmable microprocessor, or by mechanical and/or electronic logic arrangements of any suitable kind.

In view of the failure of the prior art to provide low cost systems for treating circulated air for reduction of odors or environmentally adverse elements, it is an object of the present invention to provide an apparatus which is capable of entraining liquid air treatment materials into a circulated air stream in a simple and reliable manner.

Another object of the invention is to provide an apparatus which may be added to existing air circulation systems for periodically supplying atomized treating liquid into a moving air stream.

Another object of the invention is to provide a simplified apparatus comprising a treating liquid container, a pump and motor arrangement and an atomizing discharge nozzle, and a conduit between them, together with a simplified control system for periodically discharging liquid into a fluent air stream forming a part of an air circulation system in a habitable environment.

A further object of the invention is to provide an aftermarket accessory for automobiles which includes a simple unit comprising at least one reservoir, an electrically operated pump and motor circuit, at least one discharge nozzle, means for disposing the discharge nozzle within the air circulation system of the automobile, and a conduit connecting the pump outlet to the nozzle.

Another object of the invention is to provide an apparatus which is capable of use in both the supply and return sides of an air circulation system.

Yet another object of the invention is to provide an apparatus which is able to be operated by available electrical or other power already associated with the environmental controls present in the intended application.

Another object of the invention is to provide an air treatment apparatus which is capable of reliable use at low cost and which is able to be constructed, in varying degrees of complexity, so as to operate in manual, semi-automatic, or fully automatic modes.

A further object of the invention is to provide an apparatus which will enable air freshener, air treatment chemicals or other liquids to be discharged periodically into a moving air stream, with such apparatus being able to be constructed at low cost and to operate with a high degree of reliability.

The present invention achieves these and other objects and advantages by providing an air treatment system for circulated air which includes a treating liquid container, a pump and pump actuator for withdrawing liquid from the reservoir, a discharge nozzle, a conduit extending between the pump and the nozzle, and means for mounting the discharge nozzle within a duct for circulated air, together with means for periodically actuating the pump so as to force liquid from the reservoir through the conduit and into the air stream in an atomized condition.

The manner in which the foregoing and other objects and advantages are achieved in practice and will become more clearly apparent when reference is made to the following detailed description of the preferred embodiments of the invention set forth by way of example and shown in the accompanying drawings, wherein like reference numbers indicate corresponding parts throughout.

DESCRIPTION OF THE PREFERRED EMBODIMENTS OF THE INVENTION

While the invention may be embodied in a number of different forms and used in various applications, descriptions will be given of several preferred embodiments, the first of which is a simplified form of apparatus for use in an automotive application. Other applications, including use in building structures, are described. Construction and operation of the apparatus for use in different modes is also described with reference being made to optional control and other features.

Figure 1:
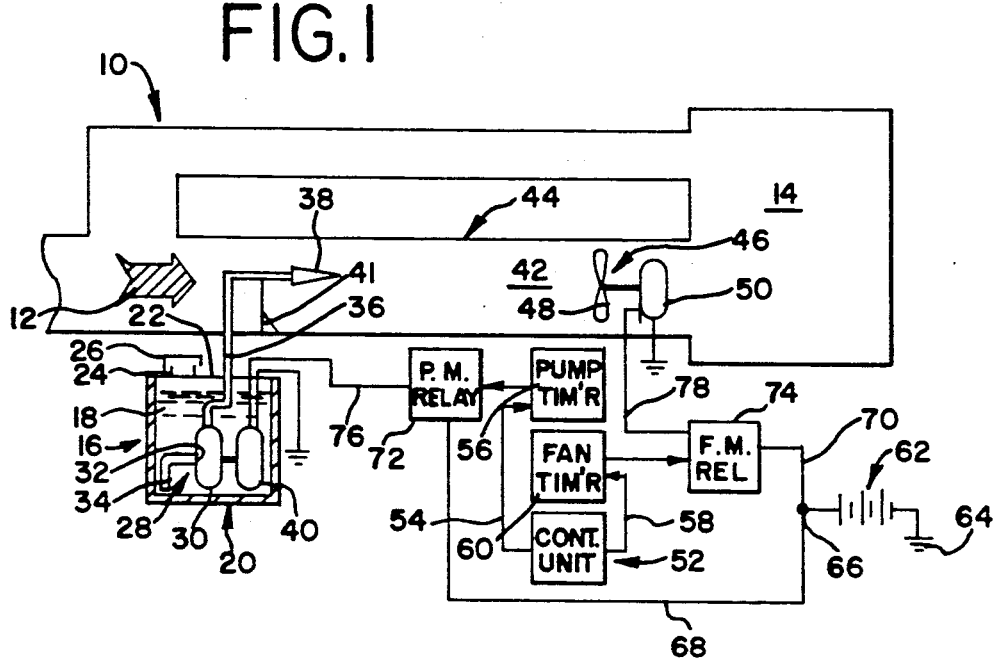
FIG. 1 is a side elevational view, partially schematic and partially in block diagram form, showing the general arrangement of a simplified form of apparatus made according to the invention.

Referring now the drawings in greater detail, FIG. 1 shows one form of the apparatus being used in an automotive application, and illustrates in a general sense certain of the principles of the invention.

Referring again to FIG. 1, for example, an air treatment apparatus generally designated 10, is shown to be made according to the invention, and to embody a number of elements in a combination which enables the apparatus to treat a supply of fresh air shown by the arrow generally designated 12 with a volatile liquid before the air is circulated to a habitable environment generally designated 14.

In the form shown, the apparatus 10 includes a container generally designated 16 for receiving a supply of volatile treating liquid 18. A combination submersible pump and electric motor generally designated 20 is shown to be disposed within the interior of the container 16; the container in turn includes a container cover 22 with a refill inlet 24 closed off by a removable cap 26. The pump and motor unit 20 includes both a pump generally designated 28 and having a housing 30, a pump inlet 32 at the upper end of a siphon or dip tube 34, the lower end of which lies near the bottom of the container 16. A liquid discharge conduit 36 extends between a portion of the pump housing 30 and a discharge spray nozzle generally designated 38. The pump 28 is driven by a d.c. electric motor generally designated 40.

The discharge nozzle 38 is secured as by mounting means in the form of a bracket 41 within the interior 42 of an air supply duct generally designated 44. According to the invention, forced air circulation within the duct 44 is achieved by the provision of a fan and motor unit generally designated 46 and shown to include a fan impeller 48 and a d.c. motor 50.

Other elements shown to be present include a control unit generally designated 52, having a lead 54 connected to a pump timer 56, as well as a lead 58 connected to a fan timer 60. As shown, a current source in the form of a battery 62 has a ground terminal at 64 and a junction at 66 from which a pump motor relay line and a fan motor relay line 68, 70 respectively extend to their associated pump motor and fan relays 72, 74. Leads 76, 78 extend from the relays 72, 74 to operate the pump motor 40 and the fan motor 50, respectively when the control unit 52 is actuated The operation of the relays and timers is discussed elsewhere herein.

Figure 2:
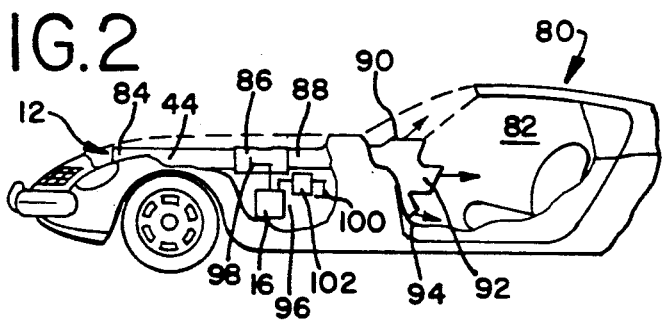
FIG. 2 is a fragmentary side elevational view, with portions broken away, showing certain elements of the air treatment apparatus of FIG. 1 embodied in a motor vehicle.

Referring now to FIG. 2, a typical application of the air treatment 10 in an automotive application is shown. In FIG. 2, in an automobile generally designated 80 the habitable environment comprises the vehicle passenger compartment 82. As shown, the underhood portions of the vehicle 80 include a duct 44 having an open front portion 84 serving as the intake for fresh air generally designated 12. As is conventional, a housing 86 disposed at the inner end of the duct 44 near or on the vehicle firewall serves to receive the heater core and the air conditioner expansion coil (not shown).

In use, the air entering the duct 44 passes through this housing wherein the air may be heated or cooled as indicated. The exact construction of this element not being an essential feature of the invention, a detailed description thereof is omitted, it being known to those skilled in the art that such constructions are conventional and that the expansion coils and heater core may be placed relatively close together, in spaced apart relation, or otherwise, and may be positioned in the same area as each other, or may be spaced apart and connected by a series of doors, ducts or the like.

In any case, an air plenum 88 is positioned downstream of the housing 86 to receive treated or conditioned air. This air, in a manner known to those skilled in the art, may enter the vehicle interior 82 through one or more ducts such as a defroster duct 90, a panel duct 92, and/or a floor duct 94. It is being understood that selecting whatever inlet passage is desired is a matter of choice to be exercised by the vehicle operator. The air passed to the interior 82 is exhausted by vent windows or otherwise, and is usually (but not always) not recirculated.

According to the invention, the treating liquid container 16 is mounted on a fire wall or other underhood portion 96 of the vehicle. A liquid conduit 98 extends from the container 16 through a sidewall of the housing 86 where it serves to direct liquid to the discharge spray nozzle (not shown in FIG. 2) as best illustrated in FIG. 1, for example. FIG. 2 also shows that a line 100 may extend from a power source (not shown) to a control and relay panel 102 or the like to actuate the pump and motor assembly shown in FIG. 1. The pump and relay panel 102 customarily houses the various timers, relays and other circuits necessary for operation of the pump and motor, while the fan motor is situated within the housing 86 or elsewhere as is conventional in normal automobile design practice.

Referring now to the operation of the apparatus 10 of the invention in the form shown in FIGS. 1 or 2, it will be assumed that it is desired to deodorize or disinfect the air passing into the vehicle interior For this purpose, the vehicle operator would actuate the control 52 which may be a push button, toggle switch or the like. According to the invention, the signal to the fan timer 60 actuates the fan to insure that air is flowing within the interior 42 of the duct 44. If the fan is not already operating, it will be energized; the fan timer insures that the fan will continue to operate for a fixed duration in excess of a given time, such as 45 seconds, for example.

At the same time, the pump timer 56 is arranged so as to afford a finite delay, such as 10 seconds, to enable the fan motor to be actuated and the fan to be operating at a speed suitable to create the desired air flow in the duct interior 42 before discharge is attempted. After this predetermined delay, the pump timer energizes the pump to deliver one or more "shots" of liquid from the container 16 to the spray nozzle 38, where it is discharged in an atomized condition. In the example given, a single continuous spray of five seconds would be appropriate. Thereafter, the pump shot timer clocks out and the pump motor relay is de-energized; the fan timer, according to this example, would call for continued operation of the fan motor for additional 30 seconds, i.e., until the entire operating duration had timed out. Thereupon, the fan motor relay would drop out and the fan would be de-energized.

As will appear, the logic of this control sequence may be altered somewhat, depending on the sophistication of the unit in question. It is strongly preferred that air flow at or beyond a predetermined threshold be required as a condition of operating the pump, and that the fan motor continue to supply such air flow well after the discharge of the volatile liquid. In the example given, the liquid is an aqueous solution of a deodorizing liquid containing a minor proportion of alcohol and chlorophyll, or other chemical composition capable of absorbing or neutralizing odors, such as smoke or the like.

Figure 3:
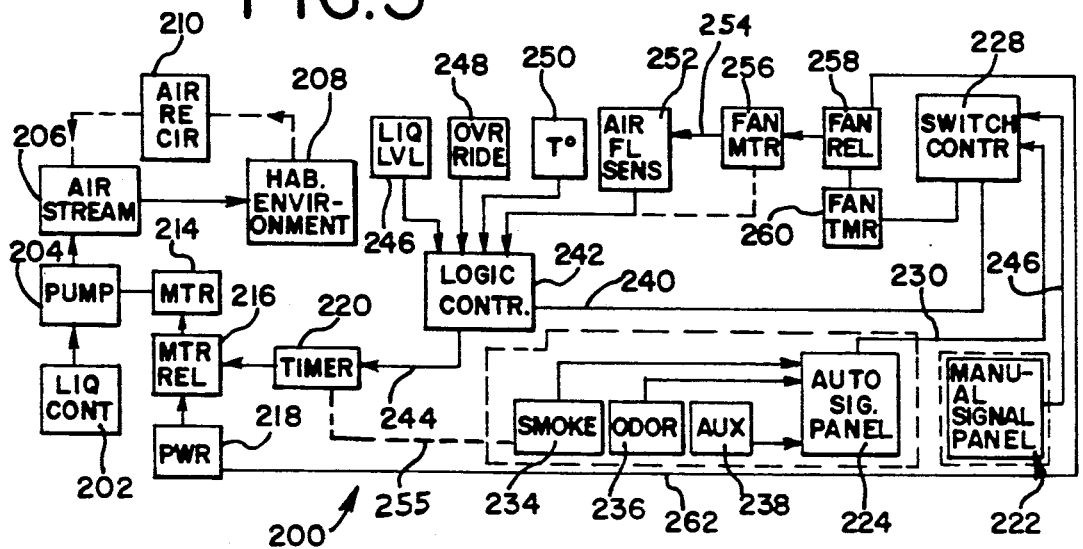
FIG. 3 is a block diagram showing various control and power arrangements available for use in controlling the air treatment system of the invention, also showing in block diagram form the manner in which the air is treated.

Referring now to FIG. 3, another form of control system is illustrated for use with the invention. This system, generally designated 200, includes a number of optional features. For purposes of clarity, different numbers are given to the elements of this system, although their counterparts may, in some cases, be found in the simplified control system illustrated in FIG. 1.

In FIG. 3, a power source is illustrated, but not all of the control return lines or grounds are shown, it being understood that the apparatus would be wired in a conventional way known to those skilled in the art. In the form shown in FIG. 3, a direct current source is shown with particularity, but it is understood that the system is adaptable to alternating current and that a.c. or combination of a.c. and d.c. controls, drives and the like may be provided if this is indicated for some reason. The invention does not depend for its novelty on the type of energy used to actuate the controls in question.

Referring now in greater detail to FIG. 3, the control system 200 is shown to include a liquid reservoir 202 and a pump 204. An air stream is schematically represented at 206. As shown, a habitable environment 208 may not only receive air from the air stream 206, but air recirculation means 210 may be provided to withdraw air from the environment 208 and supply it as through a return air duct 212 to the incoming air stream 206. Thus, the pump is shown to be capable of discharging liquid into the air stream, whether or not that air stream comprises new air or recirculated air.

Further according to the embodiment of FIG. 3, a motor 214 drives the pump 204, and the motor is driven by current passing through relay 216 from a current source 218. Actuation of the relay 216 is controlled by a motor timer 220. In further keeping with the form of apparatus shown in FIG. 3, there are shown both a manual signal control panel 222 and an automatic signal control panel 224. A signal line 226 extends from the manual signal control panel to the switch control 228, and a signal line 230 extends from the automatic signal panel 230 to the switch control 228.

In the automatic system 224, various inputs such as a smoke presence detector 234, an odor presence detector 236, and an auxiliary input 238 are shown. A smoke and odor detector may be of any kind, and are shown schematically as being operatively connected to the panel such that the detected condition will provide a signal calling for the air treatment system to be energized.

The auxiliary function control 238 may be of any desired kind, such as a separate timer, which operates periodically, an actuator which is energized upon starting the vehicle or the like. The signal panel may require the presence of two or more conditions to call for energizing the switch.

Referring now to the switch control 228, it will be noted that this unit 228 includes a line 240 extending to and connected with the logic control panel 242. The logic control is described as an enable/disable control which, upon generation of an enabling signal, transmits the signal through the line 244 to the pump motor timer 220. Inasmuch as the enable/disable logic control is intended to serve several functions, it may require some or all of the various inputs which are shown in FIG. 3. For example, a liquid level detector 246, an override control 248, a temperature sensor 250 and an air flow sensor 252 are shown as shown as inputs to the logic control 242. The air flow sensor unit 252 is shown as including a line 254 extending from the fan motor circuit 256, for reasons which will appear. As is further shown in FIG. 3, a fan relay 258 and a fan timer 260 are associated with the switch control 228; a power line 262 connects the power source 218 to the fan motor 256 through the fan relay 258.

Assuming now that it is desired to operate the air treatment apparatus 200, it will be assumed that the power unit 218 is a vehicle battery which is adequately charged. The operation of the apparatus in the manual control mode will be described first Assuming the operator energizes the button on the signal panel 222, the switch control is enabled and an enable signal is sent to the logic control unit 242. The switch control also energizes the fan relay 258 and the fan timer 260, thus energizing the fan motor 256. When the fan motor is operating with sufficient speed to meet the threshold of the air flow sensor 252, an appropriate signal is furnished to the logic control 242. Assuming that the fan relay is energized and the motor is running so as to create the necessary air flow, the fan timer 266 will insure that the fan will continue to operate for a predetermined minimum time.

Figure 4:
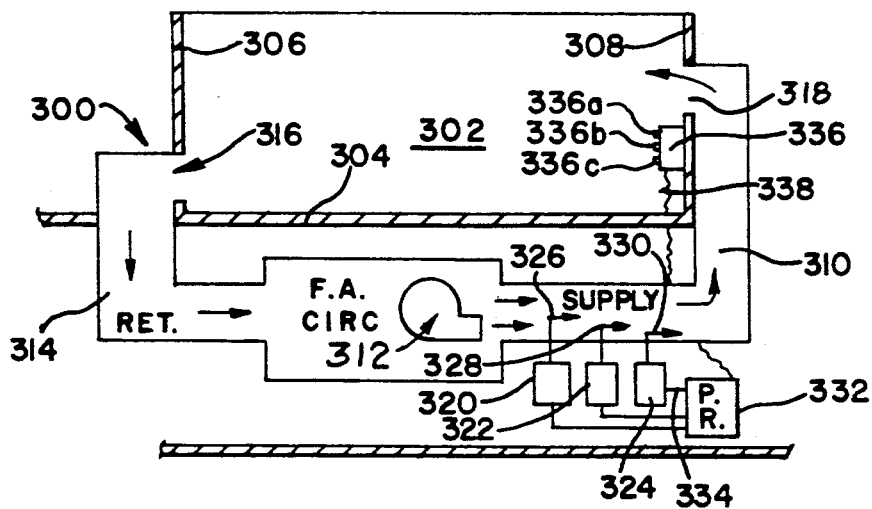
FIG. 4 is a vertical sectional view, partly diagrammatic in nature, showing the relation of one form of air treatment system made according to the invention to the air return and air supply ducts and a portion of the forced air circulation system of a habitable residential or commercial space.

Consequently, it will be assumed that the sensor 252 continues to indicate to the logic control 242 that beginning the air treatment cycle is permitted. A signal through line 244 to the timer 240 is thus enabled in the presence of positive signals from the air flow sensor and the switch control lines. The signal does not pass to the timer until the air flow sensor 252 determines that air flow conditions are favorable. The timer 220, however, is a duration timer which is manually or automatically set to control the duration of liquid discharge in this embodiment. The signal then passes from the timer 220 to the relay 216; when energized, the relay connects the current source 218 and the motor 214 to actuate the liquid pump and hence discharge a continuing stream of volatile liquid into the air stream 206. At a present time after the shot size timer 220 has timed out, the fan timer 260 will no longer call for fan power, and the system reverts to its passive state, awaiting subsequent manual energization.

Referring now to operation in the automatic mode, portions relating to the fan circuit and air flow sensor remain the same, as does the operation of the shot size timer and the pump motor relay In this connection, however, a feedback control loop 255 is shown by the broken line to connect the smoke sensor 234 to the timer, for reasons which will appear. Assuming now that the automatic signal panel 234 is in operation, it will be assumed that the auxiliary function control 238 includes a starter switch actuation detector in the timer, whereby, when the vehicle starter is engaged, a timer is actuated and, for example, one minute later, air treatment is to commence. This cycle start signal thus passes from the automatic signal panel 232 through the line 230 to the switch control 228. In this instance, the enable/-disable logic control must not only receive an appropriate signal from the air flow sensor 252, but is shown as being subject to control by the liquid level detector 246 and the temperature control 250. In this instance, assuming that the temperature is high enough to assist in volatilizing the liquid, and the liquid level is appropriate, the logic control will be enabled and liquid discharge will take place as described in the manual mode.

In the mode just described, logic is present in the auxiliary function unit 238 such that the command to discharge treating liquid will remain for a single actuation cycle. Thus, if the temperature is low, whatever elapsed time is required for the temperature to rise will not cancel the command to create liquid discharge In this instance, therefore, the discharge might occur significantly later.

Referring now to another aspect of the automatic operation, the panel 232 may include means for actuation in response to one or more other functions such as the smoke detector 234 or the odor detector 236. In this instance, when the detected condition occurs within the habitable environment 208, signals are generated and fed to the automatic panel 224, which then signals the switch control to enable the pump circuit, subject to the existence of the other conditions required by the logic control 242. The feedback loop 255 makes it possible to reset the timer 220 or keep it energized as long as the detected condition persists FIG. 3 also shows another optional feature, the override 248. This input simply eliminates inhibiting outputs which may be present from the temperature sensor or the liquid level sensor, the flow control, or other sensor, and permits what may be considered manual or semiautomatic operation.

The system just discussed, with appropriate electrical wiring, is therefore suitable for use in any habitable environment. Referring to the air flow sensor, for example, the significant air flow may not take place in a building environment without operation of a fan motor, whereas in an automotive or like application, sufficient air flow may take place, merely by reason of vehicle speed, to obviate the need for actuating the fan motor. The detector may therefore operate either as a part of the fan motor or as a flow sensor, or both.

Referring now to FIG. 4, a slightly modified form of the apparatus of the invention is shown in a building environment. Here, the apparatus generally designated 300 is shown to include a habitable interior space 302 defined by a floor 304 and a pair of building walls 306, 308. A supply air duct 310 is disposed downstream of a forced air circulation apparatus 312 which may be a furnace, a central air conditioning unit, or a combination of these elements. A return air duct 314 supplies air to the circulation system 312. A cold air register inlet 316 is provided adjacent the floor 304 in one wall 306 while an air outlet register 318 is provided adjacent the top of wall 308. According to the invention, a plurality of reservoirs 320, 322, 324 is provided, each one including its own conduit 326, 328, 330 for supplying an associated nozzle (not shown) within the interior of the air supply duct 310. The relay and control panel 332 is shown to have an operative connection 334 to the submersible pump and motor units (not shown) within the respective containers 320–324. A power source (not shown) energizes the pumps and motors upon command.

In the form of apparatus shown in FIG. 4, the control unit 336 comprises a manually operated actuator and selector having separate buttons 336A, 336B, 336C, for purposes of indicating which of the particular containers 320–324 is to supply the liquid for atomization in the air supply duct 310.

Accordingly, the illustration of FIG. 4 shows a form of the invention wherein every element except the control unit of air treatment system is disposed in the air supply or return duct in an area remote from the habitable environment 302. Under such circumstance, and particularly in the case of a residence or commercial establishment, the supply containers may be made relatively large and refilling them or replacing them periodically is done outside the habitable space at a convenient time. Naturally, an automatic control having one or more of the features described in connection with FIG. 3 may be substituted for the manual control unit 336 shown in FIG. 4.

Figure 5:
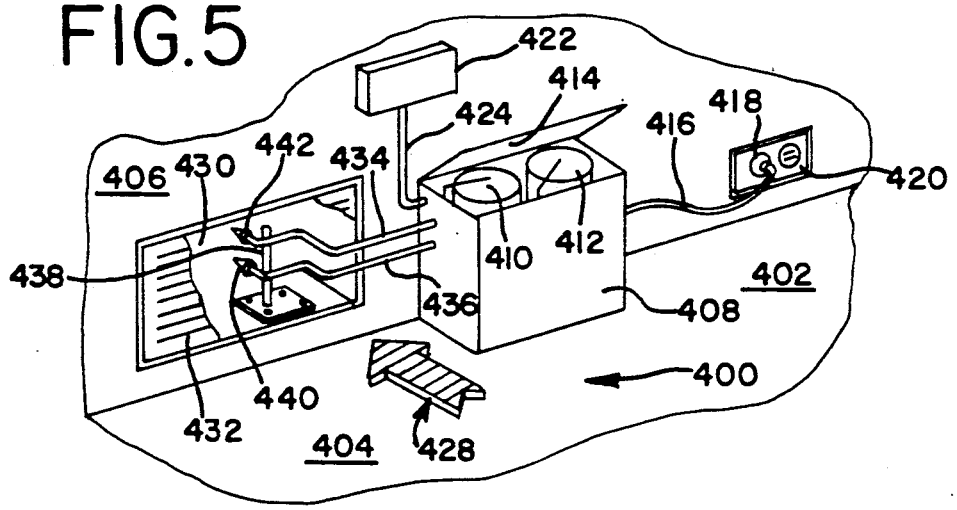
FIG. 5 is a perspective view, partly diagrammatic in nature, showing the air treatment apparatus of the invention as installed within a living space and associated with a return air duct forming a part of an air circulation system.

Referring now to FIG. 5 a further optional variation of the invention is shown. Here, the apparatus generally designated 400 is shown to be disposed within a habitable space 402 which includes a floor 404 and one or more building walls 406. In this embodiment, an exterior housing 408 contains, for example, two containers 410, 412 for treating liquids. Each of the containers include an associated dip tube, submersible pump and motor and other elements (not shown) but similar to those illustrated in connection with FIG. 1. These elements are not shown in FIG. 5 inasmuch as they do not differ from those of the earlier described embodiments. The unit 400 includes a movable cover 416 permitting the individual containers 410, 412 to be removed and replaced. According to he embodiment of FIG. 5, a power cord 416 is shown to terminate in a plug 418 which draws current from a wall plug 420. The control system is schematically illustrated as a control box 422 connected to the interior of the housing 408 by a line 424.

According to the invention, return air as shown by the arrow 428 passes into a return air duct 430 covered by a grille or screen 432. A pair of liquid conduits 434, 436 are provide, and each is associated with a respective liquid container 410, 412. Nozzles 440, 442 are positioned as by a bracket 438 within the interior of the return air duct 430. Discharge of vaporizable volatile fluid through either nozzles 440, 442 is achieved as described in the other embodiments.

The significance of the illustration of FIG. 5 is that it shows that the air treatment system may be associated with return air, as well as with supply air, and hence may be in a building which includes both supply and return air ducts. In some cases, this may be more advantageous for purposes of convenient placement of the containers or the like. The control unit 422 may be automatic, manual or semi-automatic as described in connection with the other embodiments.

Figure 6:
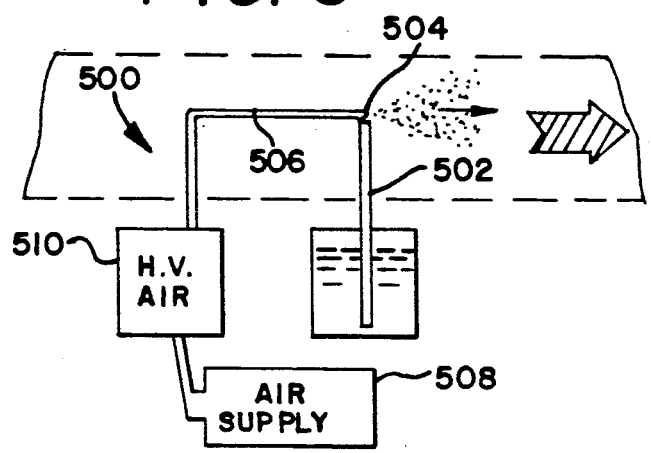
FIG. 6 is a diagrammatic view of another form of atomizer useful as a part of the invention.

Referring now to FIG. 6, an alternate form of apparatus generally designated 500 is shown. This unit is similar to the others except that an aspiration tube 502, with a small diameter orifice 504 at its outlet is provided. A tube 506 serves as a source 510 of high velocity air coming from a supply 508 such as a compressed air tank. In this example, instead of using a positive displacement pump, or the like, the entrainment of vaporizable fluid in the air stream is secured by passing an air stream over the upper end portion 504 of the aspiration tube 502. The pressure differential created by the rapid discharge of air draws volatile liquid through the aspiration tube to achieve the atomization in this way.

The use of this form of atomizer is not preferred for most applications, but may be appropriate where a compressed air source is available, such as, for example, vehicles with air brakes, or within an industrial environment, where "shop" air is present, for example.

It will thus be seen that the present invention provides a new and improved air treatment apparatus having a number of novel advantages and characteristics, including those referred to specifically herein and others which are inherent in the invention. Several preferred embodiments of the invention having been described in detail by way of example, it is anticipated that the variations in the described forms may occur to those skilled in the art, and that such variations may be made without departing from the spirit of the invention or the scope of the appended claims.

We claim:

1. An apparatus for supplying treated air to the interior of an automotive vehicle which includes a forced air circulation system and a temperature control system, said forced air circulation system including an air supply conduit having one of its ends exposed to the atmosphere exterior to the vehicle and the other of its ends terminating in a plurality of vehicle interior ducts and outlets, and a fan and motor operatively associated with said air supply conduit so as to impart forced movement to air within said conduit, said temperature control system including heater core and an evaporator coil each having portions disposed within said conduit, said apparatus further including an air treatment system for discharging a vaporizable liquid into said air supply conduit downstream of said heater core and said evaporator coil, said air treatment system including at least one container for receiving a supply of vaporizable liquid, a liquid pump having a pump inlet, a pump outlet, a pump motor, an atomizing nozzle, and a liquid line extending from said pump outlet to said atomizing nozzle, means for energizing said liquid pump motor and a control circuit for said pump motor energizing means, said control circuit comprising, in combination, a main operating control, means for signaling said operating control that said liquid is to be discharged, separate air flow and temperature sensing means, a pump timer and a logic control unit, said logic control including means for generating an output signal to enable said pump timer to be alternately energized and de-energized, said logic control being operable to energize said pump motor timer only in the conjunctive presence of a positive signal from said main control and from said air flow and temperature sensing means, whereby, when said signaling means is energized, said pump will operate for a controlled time to cause said volatile liquid to be taken from said container and be discharged into said conduit through said atomizing nozzle, provided that said logic control is receiving input signals from said air flow and temperature sensors and said main operating control operating control.

2. An apparatus as defined in claim 1 wherein said signaling means is manually operable.

3. An apparatus as defined in claim 1 wherein said signaling means is operable in response to detection of a condition with the interior of said vehicle.

4. An apparatus as defined in claim 1 which further includes a relay for operating said liquid pump.

5. An apparatus as defined in claim 1 wherein said main switch further includes means for energizing said fan motor.

* * * * *